United States Patent [19]
Bartsch

[11] Patent Number: 4,760,085
[45] Date of Patent: Jul. 26, 1988

[54] USE OF D,L- AND D-CARAZOLOL AS ANTI-GLAUCOMA AGENT

[75] Inventor: Wolfgang Bartsch, Viernheim, Fed. Rep. of Germany

[73] Assignee: Boehringer Mannheim GmbH, Mannheim, Fed. Rep. of Germany

[21] Appl. No.: 35,231

[22] Filed: Apr. 6, 1987

Related U.S. Application Data

[63] Continuation of Ser. No. 568,437, Jan. 5, 1984, abandoned.

[30] Foreign Application Priority Data

Jan. 13, 1983 [DE] Fed. Rep. of Germany ....... 3300933

[51] Int. Cl.⁴ .............................................. A61K 31/40
[52] U.S. Cl. .................................... 514/411; 548/444
[58] Field of Search ...................... 548/444; 514/411

[56] References Cited

U.S. PATENT DOCUMENTS 4,503,067 3/1985 Wiedemann ....................... 548/444

FOREIGN PATENT DOCUMENTS 1369580 10/1974 United Kingdom .

OTHER PUBLICATIONS

*The Merck Index,* 9th ed. (1976), No. 9170.
*The Merck Index,* 10th ed., (1983), No. 1753.
*AMA Drug Evaluations,* 5th ed., (4–1983), p. 457.
Manalan et al., Circ. Res. 49: 326–336 (1981).

*Primary Examiner*—Robert W. Ramsuer
*Attorney, Agent, or Firm*—Felfe & Lynch

[57] ABSTRACT

The present invention is concerned with the topical use of D,L- and D-carazolol and of the pharmacologically acceptable salts in the therapy of glaucoma. The present invention is also concerned with eye drops containing these active materials.

13 Claims, No Drawings

USE OF D,L-AND D-CARAZOLOL AS ANTI-GLAUCOMA AGENT

This is a continuation of application Ser. No. 568,437, filed 1-5-84, now abandoned.

The present invention is concerned with the use of an isopropylaminopropanol derivative and of pharmacologically acceptable salts thereof for the treatment of glaucoma and with eye drops containing this derivative and/or pharmacologically acceptable salts thereof.

Carazolol is the internationally accepted generic name for racemic (D,L)-1-carbazolyl-(4)-oxy-3-isopropylaminopropan-2-ol. Its outstanding $\beta$-blocking action in humans and animals is well documented.

This compound was described for the first time in Example 1 of Federal Republic of Germany Patent Specification No. 22 40 599. In a number of further publications, the $\beta$-blocking action was ascertained in comparison with known $\beta$-blockers (see W. Bartsch et al., Arzneim.-Forsch., 27(I), 5, 1022 et seq.; W. Bartsch et al., Excerpta medica, pub. Amsterdam, 1980, pp. 44 et seq.). D,L-Carazolol is known under the Registered Trade Mark "Suacron" as a $\beta$-receptor blocker in veterinary medicine and under the Registered Trade Mark "Conducton" for use in human medicine.

Surprisingly, we have now found that D,L-carazolol can also be used in the treatment of diseases of the eye in extremely low concentrations, namely, for reducing the internal pressure of the eye in the therapy of glaucoma.

It has already been known for a long time that $\beta$-receptor blockers, such as propranolol and the like, can reduce the pressure of the eye in glaucoma patients (cf. G.K. Krieglstein, Klin. Monatsblatter fur Augenheilkunde, 172, 677 et seq/1978). However, in the case of local use, $\beta$-blockers display unpleasant side effects which result in burning and prickling pains of the eyes and also bring about a superficial anaesthesia of the eyes. $\beta$-Blockers of this type are, therefore, less suitable for glaucoma therapy.

Timolol, i.e. S-(-)-1-(tert.-butylamino)-3-[(4-morpholino-1,2,5-thiadiazol-3-yl)-oxy]-propan-2-ol, which is used for glaucoma therapy, displays, in the commercially available form (0.5% solution), especially in long-term therapy, side effects such as a significant lowering of the blood pressure and the development of dry eyes (see N.V. Nielsen, Z. prakt. Augenheilkunde, 2, 71-77/1981).

However, experiments with D,L-carazolol showed that a significant lowering of the inner pressure of the eye is achieved even with a 0.01% solution of D,L-carazolol, without any undesired side effects being observed at this dosage, in spite of the high therapeutic effectiveness.

Thus, the present invention is concerned with the use of racemic D,L-carazolol for the treatment of glaucoma, as well as with pharmaceutical compositions containing D,L-carazolol for topical use in eyes.

It has been ascertained experimentally that, in general, a $\beta$-blocking quality is associated with the L-isomeric form (see A.M. Barrett et al., Brit. J. Pharmac., 34, 43-55/1968). This also applies to carazolol. Rare but very serious incidents arising after the administration of timolol (L-isomeric form) as a result of the $\beta$-blockade include asthmatic attacks, heart rhythm disturbances and even some fatal cases, all of which have been described in the literature (see A. Vonwil et al., Schweiz. med. Wschr., 111, 665-669/1981). We have now found that, in the case of D-carazolol, a therapeutic action is also present, namely, a significant lowering of the internal pressure of the eye, without the occurrence of systemic side effects which are typical of $\beta$-blockers.

Consequently, the present invention is also concerned with the use of D-carazolol as an anti-glaucoma agent, with the use thereof and with pharmaceutical agents which contain D-carazolol practically free from L-carazolol for topical use in eyes.

D-Carazolol, which is also called R(+)-carazolol, was investigated by S. Manulan et al. for its $\beta$-blocking action (see Circ. Res., 49, 326-336/1981) but no such action was ascertained.

For the treatment of glaucoma, D,L- and D-carazolol and the pharmacologically acceptable salts thereof are used in the form of eye drops. Preferred salts are those with physiologically compatible inorganic and organic acids, for example hydrochloric acid, hydrobromic acid, phosphoric acid, sulphuric acid, acetic acid, salicylic acid, citric acid, benzoic acid, naphthoic acid, 2-acetoxybenzoic acid, adipic acid and maleic acid.

Isotonic solutions are preferred with a pH of about 7.0. As the medium therefor, it is preferred to use water, which can contain conventional additives, for example preserving agents, solubilizing agents and buffers. Preferred preserving agents include benzyl alcohol, benzalkonium chloride, phenol and chlorohexidine acetate. Preferred solubilising agents include, in particular, polyethylene glycols, polyvinylpyrrolidone and glycerol. As buffer, it is preferred to use acetic acid/sodium acetate, citric acid/sodium citrate or sodium ethylenediaminetetraacetate.

Investigations on humans have shown that racemic D,L-carazolol and the salts thereof have a good compatibility and significantly lower the internal eye pressure in glaucoma patients, even at a concentration of 0.005 to 0.03%. For this purpose, patients were treated once per day with D,L-carazolol eye drops. An especially preferable formulation was found to be a 0.01% solution, which did not give rise to any of the known side effects, such as an anaesthetised feeling in the eye or in the head region and a strong burning sensation.

In the case of the use of D-carazolol and of the salts thereof, there was determined a corresponding significant lowering of the internal eye pressure and in no case were side effects observed. In anti-glaucoma formulations, D-carazolol was employed in concentrations of 0.001 to 0.1% and preferably of 0.005 to 0.01%.

The dosage, expressed as the amount of eye drops required per day, depends upon the concentration of the solutions used. As a rule, one drop of a 0.01% D,L-carazolol or of a 0.005% D-carazolol solution per eye twice a day should suffice but it is also possible to use 3 to 4 drops per day of a solution of lower concentration.

The following Examples, which are given for the purpose of illustrating the present invention, describe the preparation of D-carazolol in the form of its hydrogen acetate, as well as of eye drops containing D,L- and D-carazolol as active material:

EXAMPLE 1

Preparation of R(+)-1-carbazolyl-(4)-oxy-3-isopropylaminopropan-2-ol hydrogen acetate (D-carazolol hydrogen acetate).

178.8 g. (0.6 mol) D,L-carazolol, 62.1 g. (0.3 mol) L-N-acetylphenylalanine (LAP) and 18 g. (0.3 mol)

glacial acetic acid are heated to the boil in 4.5 litres of water, a substantially clear solution being obtained. This is filtered through a fluted filter paper and stirred until cold, without external cooling.

As soon as the solution begins to become turbid at about 65° C., it is seeded with some LAP/D-carazolol salt. Cooling to ambient temperature is allowed to take place and the product obtained is then filtered off with suction.

The moist product is dissolved in 2250 ml. hot water, filtered through a fluted filter paper, again cooled to ambient temperature while stirring and the precipitated product is filtered off with suction. After again recrystallising from 1800 ml. and 600 ml. water, the moist product (172 g.) is shaken up in 1.5 litres ethyl acetate and 1.5 litres 1n aqueous sodium hydroxide solution until two clear phases are formed. After phase separation, the ethyl acetate phase is shaken out three times with 450 ml. amounts of water, dried over anhydrous sodium sulphate and evaporated in a vacuum at a bath temperature of about 50° C.

The residue obtained (43.2 g.) is recrystallised from 330 ml. boiling toluene, with the addition of a trace of active charcoal. The solution is allowed to cool to ambient temperature without external cooling, then stirred for 1 to 2 hours in an ice-bath, filtered off with suction and dried at 60° C. in a circulating current of air.

The product obtained is dissolved in a mixture of 600 ml. toluene and 11 ml. n-butanol while heating to about 65° C. and stirred overnight until cooled to ambient temperature. The product is filtered off with suction and thereafter washed with a little toluene. This procedure is repeated several times. Subsequently, the product is dissolved in hot ethyl acetate and mixed with glacial acetic acid. The crystallisate obtained is again recrystallised from ethyl acetate, with the addition of methanol. There is obtained pure R(+)-1-carbazolyl-(4)-oxy-3-isopropylaminopropan-2-ol (D-carazolol) in the form of its hydrogen acetate; m.p. 158°–160° C.; $[\alpha]_D^{20} = -18.8°$ (c.=1; methanol); optical purity according to GC findings 99.5%.

EXAMPLE 2

A 0.01% solution of D,L-carazolol for the topical treatment of glaucoma is prepared from:
chlorohexidine acetate: 0.10 mg.
sodium acetate trihydrate: 18.8 mg.
acetic acid: 1 mg.
D,L-carazolol: 0.1 mg.
distilled water: ad 1000 mg.

In the same way, there are obtained 0.03% and 0.005% solutions of D,L-carazolol when using 0.3 and 0.05 mg. D,L-carazolol, respectively.

EXAMPLE 3

0.1, 0.01, 0.005 and 0.001% solutions of D-carazolol are obtained analogously to Example 2 when using 1.0, 0.1, 0.05 and 0.01 mg. of D-carazolol, respectively, as active material.

TEST REPORT

D,L-Carazolol, D-carazolol and L-carazolol were tested in respect to a β-blocking and intraocular pressure-reducing activity. The β-blocking activity was measured by means of a tachycardic effect caused by 1 μg/kg i.v. isoprenaline (Dr. Bartsch et al in Drug Research 27 (I), 5, p. 1022 et seq (1977).

For measurement of an intraocular pressure-reducing effect the intraocular pressure in some test animals (rabbits) were increased by means of water loading (Method: Th. McDonalds et al in Arch. Ophtal. 82, p. 381, 1969).

Thereafter the influence of one drop of a 0,05% solution of D,L-carazolol respectively the enantiomeres thereof were measured.

| Results of experiments in conscious rabbits | | |
| --- | --- | --- |
| Substance | Reduction of the intraocular pressure in water loaded rabbits after administration of 0.05% solution | β-blocking activity $ID_{50}$ - mcg/kg i.v. - (inhibition dose 50% of the tachycardic effect of 1 mcg/kg i.v. Isoprenaline) |
| D,L-Carazolol | 12% | 3 |
| L-Carazolol | 5% | 1,6 |
| D-Carazolol | 21% | 222 |

RESULTS

The table shows the equipotent β-blocking inhibition dose ($ID_{50}$=inhibition dose 50%) as well as the reduction of the intraocular pressure in water loaded rabbits after administering of one drop of a 0,05% solution of D,L-carazolol, D-carazolol and L-carazolol.

The evaluation of these tests exhibits the following unexpected results:

1. All 3 compounds possess an intraocular pressure-reducing activity. The most effective compound is D-carazolol (21%).

2. D,L-carazolol and L-carazolol show a good β-blocking activity.

3. L-carazolol has only a small, disregardable β-blocking activity.

It will be understood that the specification and examples are illustrative but not limitative of the present invention and that other embodiments within the spirit and scope of the invention will suggest themselves to those skilled in the art.

What is claimed is:

1. Method for treating glaucoma comprising topically administering to eyes of a patient with glaucoma an effective amount of D-carazolol or a pharmaceutically acceptable salt thereof, said D-carazolol substantially free of L-carazolol.

2. Method of claim 1, wherein said D-carazolol is administered in the form of eyedrops.

3. Method of claim 1, wherein said D-carazolol is administered in the form of a composition combined with a pharmaceutically acceptable carrier.

4. Method of claim 3, wherein said pharmaceutically acceptable carrier is an isotonic solution.

5. Method of claim 3, wherein said D-carazolol comprises 0.001 to 0.1% by weight of said composition.

6. Method of claim 1, wherein said pharmaceutically acceptable salt is a hydrochloric acid, hydrobromic acid, phosphoric acid, sulphuric acid, acetic acid, salicyclic acid, citric acid, benzoic acid, napthoic acid, 2-acetoxybenzoic acid, adipic acid, or maleic acid salt.

7. Method of claim 3, wherein said composition further comprises a preserving agent.

8. Method of claim 7, wherein said preserving agent is bensyl alcohol, bensalkonium chloride, phenol, or chlorohexidine acetate.

9. Method of claim 3, wherein said composition further comprises a solubilizing agent.

10. Method of claim 9, wherein said solubilizing agent is polyethylene glycol, polyvinylpyrolidone, or glycerol.

11. Method of claim 3, wherein said composition further comprises a buffer at pH 7.

12. Method of claim 11, wherein said buffer is acetic acid/sodium citrate, or sodium ethylenediaminetetraacetate.

13. Method for treating glaucoma comprising topically administering to eyes of a patient with glaucoma an effective amount of a composition containing from 0.005 to 0.03% by weight of D,L-carazolol or a pharmaceutically acceptable salt thereof.

* * * * *